(12) United States Patent
Solomon et al.

(10) Patent No.: US 7,060,172 B1
(45) Date of Patent: Jun. 13, 2006

(54) ELECTROPHORESIS GEL AND GEL-FORMING APPARATUS

(75) Inventors: David Solomon, Officer (AU); Grace Chan, Highton (AU)

(73) Assignee: Life Therapeutics Limited, Frenchs Forest (AU)

( * ) Notice: Subject to any disclaimer, the term of this patent is extended or adjusted under 35 U.S.C. 154(b) by 0 days.

(21) Appl. No.: 09/647,821

(22) PCT Filed: Apr. 9, 1999

(86) PCT No.: PCT/AU99/00267

§ 371 (c)(1),
(2), (4) Date: Jan. 16, 2001

(87) PCT Pub. No.: WO99/53303

PCT Pub. Date: Oct. 21, 1999

(30) Foreign Application Priority Data

Apr. 9, 1998 (AU) .................................... PP2902

(51) Int. Cl.
*C07K 1/26* (2006.01)

(52) U.S. Cl. .................. 204/456; 204/465; 204/467; 204/606; 204/619

(58) Field of Classification Search ............... 204/456, 204/465, 467, 606, 619
See application file for complete search history.

(56) References Cited

U.S. PATENT DOCUMENTS

| | | | | |
|---|---|---|---|---|
| 3,814,678 A | * | 6/1974 | Fletcher | 204/450 |
| 5,061,355 A | | 10/1991 | Rose, Jr. | 204/182.8 |
| 5,350,552 A | * | 9/1994 | Ebata et al. | 264/102 |
| 5,587,061 A | | 12/1996 | Chen | 204/613 |
| 5,632,877 A | | 5/1997 | Van Atta | 204/618 |

OTHER PUBLICATIONS

Derwent Abstract Accession No. 89-006587/01, SU 1404916 A (A Med Genetics Inst) Jun. 23, 1988.

* cited by examiner

*Primary Examiner*—Ling-Sui Choi
(74) *Attorney, Agent, or Firm*—Cooley Godward LLP

(57) ABSTRACT

The apparatus includes a container (20) having a base (22) and sides (32) adapted to receive a plurality of plastic gel cassettes. An inlet port (12) is positioned in the base of the container and in fluid communication with the chamber and a baffle (11) is positioned over the inlet port, such that, in use, when gel forming fluid passes through the inlet port into the chamber, the baffle substantially reduces fluid turbulence and vertical fluid movement in the vicinity of the inlet port during flow of the fluid into the chamber. Pretreatment of the plastic cassette to remove polymerisation inhibitors prior to filling the same with fluid is by exhaustive vacuum treatment, optionally with nitrogen gas purging. This can be achieved conveniently using a vacuum chamber in which one or more plastic cassettes are placed. Optionally the vacuum chamber may be the container in which the cassettes are filled with fluid. No barrier films or chemical scavengers are required.

18 Claims, 9 Drawing Sheets

ELECTROPHORESIS GEL AND GEL-FORMING APPARATUS

TECHNICAL FIELD

The present invention relates to electrophoresis gel formation and apparatus suitable for forming gels.

BACKGROUND ART

The preparation of polyacrylamide-based matrices for electrophoresis has conventionally involved the aqueous copolymerisation of acrylamide with a crosslinking agent by free radical chemistry. The free radical polymerisation can be initiated by various processes, and once commenced, the polymerisation reaction proceeds until a gel is formed. Gels are often prepared on an individual basis prior to use, and there can be variations between gels that have been cast separately such that comparison between separations using the same gel type are not reliable. Additionally, there has now been a move to the commercial preparation of pre-formed gels which should have consistent quality and stable physical characteristics between batches.

Traditionally, polyacrylamide gels have been prepared in glass supports. For commercialisation purposes, synthetic electrophoresis gel supports offer a number of advantages over the traditional supports. These include versatility in processing, light weight properties, improved visual appearance, and shatter resistance.

It has long been recognised that the polymerisation and copolymerisation of acrylamide by free radical chemistry is subject to inhibition by a range of compounds. Specifically, oxygen acts to terminate growing polymer chains resulting in longer polymerisation times. Work by other commercial corporations (Daiichi Pure Chemicals and Novel Experimental Technologies) has recognised the impact of such inhibitors and have attempted to address the issues associated with them.

U.S. Pat. No. 5,350,552 (Daiichi Pure Chemicals) describe a batch process in which polyacrylamide gels for electrophoresis are prepared in a container with a low oxygen atmosphere. The batch process involves placing gel supporting plates into the container, in which they are separated by the aid of partition members. The purpose of the partition members is to act as "polymerisation prevention plates" to assist in enhancing and speeding up the cleaning and processing of the gels with a minimum of gel rejection. The partition members are also used to dissipate the polymerisation exotherm, which is thought to ultimately limit the batch size (up to a maximum of 50 Evalu cassettes in the batch). The partition members may be made from a variety of synthetic materials such as polyolefins, polystyrene or fluorinated resins, or from rubber, but should be able to "embrace a large amount of oxygen around its surface with high radical absorptivity." The gel support plates themselves may be made out of glass or plastic.

In U.S. Pat. No. 5,350,552, the inventors recognised the requirement of preparing the gels in a low oxygen environment in order to eliminate the appearance of "flaws or stripes" in the gel. The minimisation of flaws in the gel has traditionally been achieved by the use of an overlay solution, which is employed to prevent the re-absorption of oxygen from the atmosphere by the top portion of the gel. The use of such conditions emphasise that oxygen in the container is a problem, and removal of the oxygen is possible either through application of a vacuum or by displacement with an oxygen-free gas such as nitrogen. After the container is filled with nitrogen, the gel solution is introduced. However, it is not specified whether nitrogen flow is maintained during the polymerisation.

U.S. Pat. No. 5,685,967 (Novel Experimental Technologies) describes a process by which a mould for an electrophoresis gel is coated with barrier films, such as silicone oxide, in order to form a polyacrylamide gel suitable for biological separations. Examples are given in the body of this patent in which various plastic materials, coated and uncoated, were examined for their influence on the gel polymerisation, the resultant physical properties and separation. As an illustration, uncoated SAN (styrene-acrylonitrile) cassettes induced poor polymerisation, and correspondingly, poor electrophoresis results. When the SAN material was coated with PET-SiOx film, the gel quality and performance improved significantly. It was also noted that the oxygen permeability and transmission of the surface in contact with the polymerising solution was an important factor for consideration. This observation is related to an earlier patent specification (WO 90/13020) in which the oxygen permeability of various plastics (PMMA, PET, polystyrene, polycarbonate and polyethylene) and the implication of oxygen in the plastic is discussed.

The present inventors have now obtained improved electrophoresis gels without the aid of barrier films or chemical treatments. Furthermore, large batch production of gels has been achieved by the use of a new gel-forming apparatus.

DISCLOSURE OF INVENTION

In a first aspect, the present invention consists in an apparatus for forming electrophoresis gels, the apparatus including a container having a base and sides, the container being adapted to receive a plurality of gel cassettes; an inlet port positioned in the base of the container and in fluid communication with the chamber; and a baffle positioned over the inlet port, such that, in use, when fluid passes through the inlet port into the chamber, the baffle substantially reduces fluid turbulence and vertical fluid movement in the vicinity of the inlet port during flow of the fluid into the chamber.

Additionally, other methods of decreasing solution flow turbulence may be used if required, for example a honeycomb or mesh insert or structure may be positioned over the inlet port.

The apparatus may be of any configuration, however, the present inventors have found that a container with a substantially square shaped base is particularly suitable. The inlet port is preferably positioned in the middle of the base of the container with the baffle placed directly over the port. Preferably, the baffle has substantially the same cross-sectional shape as that of the container but of smaller dimension to allow fluid to pass around and over the baffle. The baffle is preferably flat and relatively thin in cross-section to minimise flow turbulence as fluid passes around and over the baffle. The baffle is preferably positioned above the inlet port substantially in the same plane, preferably horizontal, as the base.

Fluid may be moved into the apparatus through the inlet port by any suitable means including pumping or gravity feeding.

In one preferred form, the apparatus is placed in a vacuum chamber to assist in the formation of improved gels according to the present invention.

In a second equally preferred form, the apparatus and vacuum chamber may be combined in one vessel. The vessel may also incorporate heating and cooling means, such that the application and dissipation of heat may be used to advantageously to control the polymerisation. In addition, if necessary, further engineering refinements for automation of the processes may also be incorporated.

In order to cast a large number of gels in the apparatus, suitable racks which are adapted to hold the cassettes in the correct orientation can be placed in the apparatus.

The apparatus may further include means to control the temperature of the container to assist in the formation of suitable gels. Alternatively, the apparatus may be located in a controlled atmosphere environment.

In a second aspect, the present invention consists of an electrophoresis gel formed by the apparatus according to the first aspect of the present invention.

In a third aspect, the present invention consists of a process of forming an electrophoresis gel in a plastic cassette, the process including the steps of:

(a) pretreating the plastic cassette to substantially remove polymerisation inhibitors present therein;

(b) preparing a monomer solution of acrylamides and treating the monomer solution to substantially remove any oxygen or other gaseous polymerisation inhibitors therefrom;

(c) preparing initiator and co-initiator solutions required to induce polymerisation of the monomer solution, the solutions being treated so as to substantially remove any oxygen or other gaseous polymerisation inhibitors therefrom;

(d) mixing the monomer solution with the initiator and co-initiator solutions to form an initiated monomer solution;

(e) applying the initiated monomer solution to the plastic cassette; and (f) allowing the initiated monomer solution to polymerise in the plastic cassette.

The cassettes may be manufactured from any suitable synthetic (plastic) material, such as polyesters (PEN, PET, PETG), polyolefins (polyethylene, polypropylene), polystyrene, and any copolymers (SAN), polyacrylics(polyMMA) and any copolymers and vinylidene chloride copolymers. The different materials, however, may require different levels of pretreatment prior to gel formation.

In a preferred embodiment of the third aspect of the present invention, the pretreatment of the plastic cassette is by exhaustive vacuum treatment, optionally with inert gas purging. This can be achieved conveniently using a vacuum chamber in which one or more plastic cassettes are placed. A vacuum is then applied to the chamber with optional inert gas purging, preferably with nitrogen, if required. The time required to substantially remove polymerisation inhibitors will depend on the type of plastic used. The present inventors have found that pretreatment times from 1 to 12 hours have been particularly successful. It will be appreciated, however, that pretreatment times may vary depending on the type of plastic used and the number of cassettes being pretreated.

In order to remove oxygen and other gaseous polymerisation inhibitors from the various solutions, degassing and optional gas purging have also been found to be particularly suitable. In step (c), one means of ensuring the removal of any oxygen or other gaseous polymerisation inhibitors is to treat water, in which the solutions are made, by degassing and optional gas purging prior to adding the initiator and co-initiators to form the solutions.

In a further preferred form, step (e) applying the initiated monomer solution to the plastic cassette is carried out in the apparatus according to the first aspect of the present invention.

The gels formed may be continuous or gradient gels comprising standard gel forming ingredients having concentrations of monomer and cross-linker as presently used in standard gels known to the art.

In a fourth aspect, the present invention consists in an electrophoresis gel formed by the process according to the third aspect of the present invention.

Throughout this specification, unless the context requires otherwise, the word "comprise", or variations such as "comprises" or "comprising", will be understood to imply the inclusion of a stated element, integer or step or group of elements, integers or steps but not the exclusion of any other element, integer or step or group of elements, integers or steps.

In order that the present invention may be more clearly understood, preferred forms will be described in the following examples with reference to the accompanying drawings.

MODES FOR CARRYING OUT THE INVENTION

Figure 1:
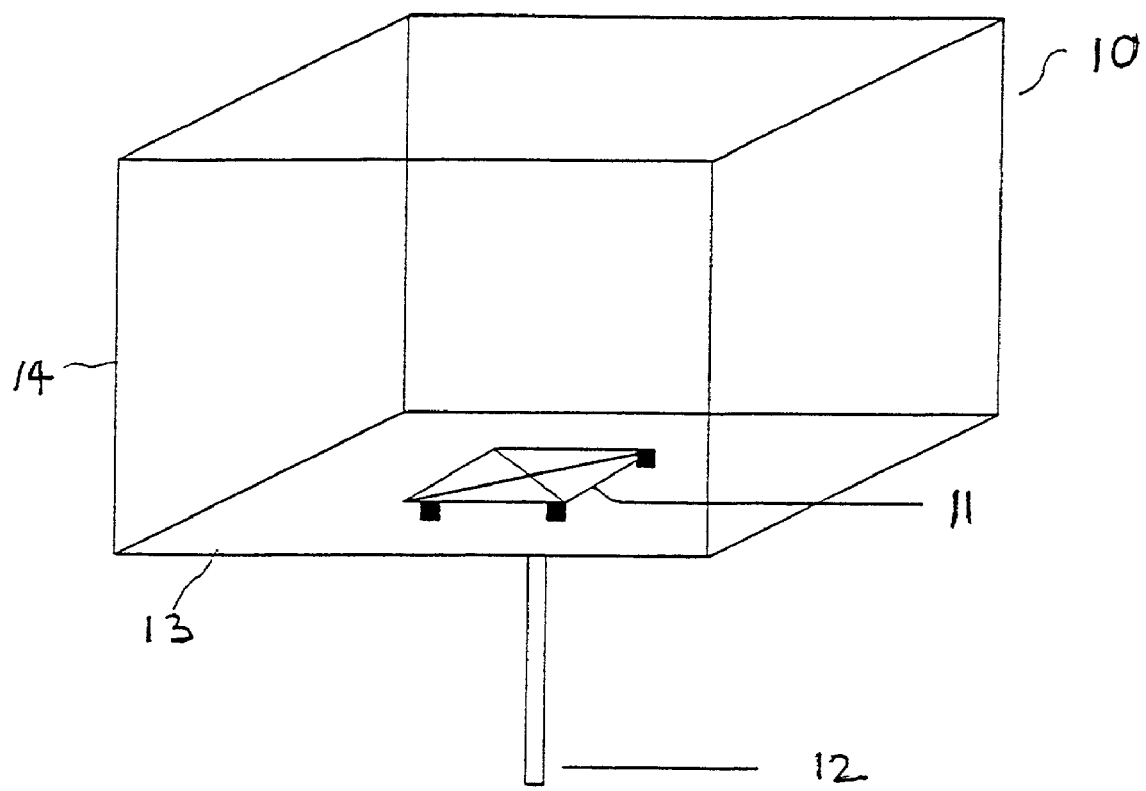
FIG. 1 is a schematic view of a gel forming tower according to the present invention.
Figure 1A:
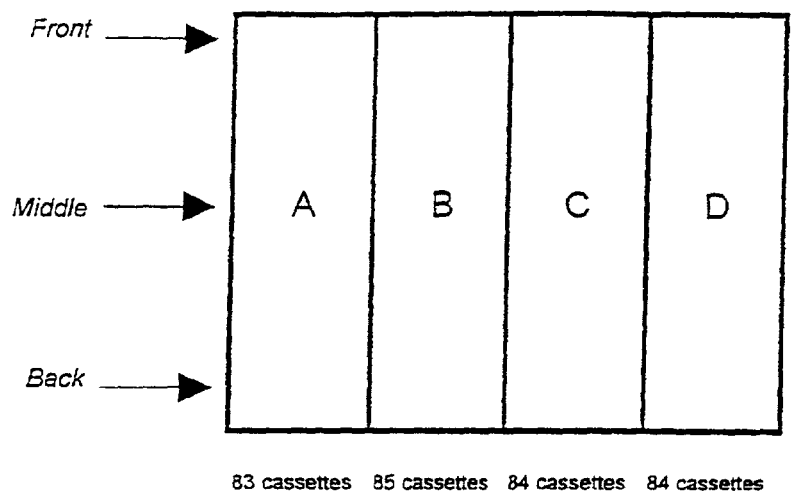
FIG. 1a is a diagram showing the positioning of four sets of gel cassettes positioned in the gel forming tower of FIG. 1.

The present inventors have developed a process in which the inhibiting properties of synthetic electrophoresis gel supports or cassettes, such as polyesters (PEN, PET and PETG), polyacrylics(polyMMA) and any copolymers, polystyrene and its copolymers (SAN) and vinylidene chloride copolymers, can be removed by an exhaustive degassing process. Under going such treatment, the gels according to the present invention prepared in plastic cassettes were equivalent to, or in some instances better than the current commercially available gels.

Furthermore, as a result of this pretreatment, the present inventors have unexpectedly found the polymerisation process required reduced quantities of initiator and co-initiator, and unexpectedly, the polymerisation exotherm of a gel is much more uniform and controlled. The gels so formed in this controlled exotherm system have greatly enhanced separating properties compared to previous gels made in plastic or in glass cassettes.

The process for the manufacture of improved polyacrylamide gels consists of several components. The components and their role in the process is outlined below:

Pretreatment Unit (Vacuum Chamber Set-Up)

This consisted of a high-vacuum chamber, into which high vacuum and an inert oxygen-free gas, preferably nitrogen, was introduced. The gel-forming container which holds the gel cassettes was placed in the chamber and a cycle of vacuum degassing and nitrogen gas purging began (evacuation/nitrogen purge). The pretreatment or degassing cycle may be a single, continuous evacuation, or may be a series of evacuation-purge cycles for a pre-determined length of time.

The pretreatment removes the inhibitors from the plastic cassettes in order to render them suitable for the polymerisation of acrylamide, and different pretreatment times are often required for different plastic cassettes. As an example, cassettes made from the polyesters polyethylene naphthoic acid (PEN) or polyethylene terephthate-co-glycol (PETG) require degassing times of 1 hour and 2 hours respectively, to produce gels of equivalent quality. Cassettes prepared from styrene-acrylonitrile copolymer (SAN) require about 12 hours degassing.

During the polymerisation of acrylamide, it is desirable to maintain an inert atmosphere in order to minimise the incorporation of oxygen and other polymerisation inhibitors into the polymer chain. For example, covalently bonded oxygen becomes a weak link in the polymer backbone as it forms a peroxide bond. Without the use of barrier films or chemical scavengers, polymerisation in synthetic gel supports was not previously thought possible, even within a low oxygen environment.

Additionally, gel polymerisations carried out previously required an organic or aqueous overlay, which can interfere with the polymerisation process. The present invention does not require such measures to obtain suitable gels.

Gel Forming Container (Tower)

Previous tower designs have been based on cubic-shaped containers or inverted pyramid designs widening out into cubic shaped area.

A tower for multiple gel casting should satisfy various requirements including having:
  minimum hold-up volume
  minimum time from the point of initiation to introduction of the solution into the cassettes
  non turbulent flow in the tower and cassettes This has been achieved in the present invention by the use of a tower design which is cubic shaped in which there is a minimum hold-up volume in the area under the level of the plastic cassettes (FIG. 1). An inner frame (not shown) on which the cassettes rest may also form part of the tower design, but may not be necessary and its use is dependant upon need and scale. The tower (10) and inner frame may be formed from any material which is not free radical inhibiting and does not interfere with the polymerisation process or solution flow. The tower (10) is preferably made from perspex for ease of processing and visual appeal. It will be appreciated that the tower may also be made of metal including suitable alloys, with or without suitable coatings.

The tower design also encompasses the use of a distributor plate or baffle (12), preferably substantially square in shape with a base (13) and walls (14), of specific dimensions ¼ to ½ way to the cross sectional diameter of the base of the tower, preferably ⅓ of the way, which is placed over the solution inlet port (12). The use of the plate (12) enables a smooth and even flow of the solutions into the tower by dramatically decreasing the vertical velocity of incoming solutions. Thus, particularly for the formation of gradient gels, disturbance to the pre-formed gradient is minimised. This has been evidenced by dye flow tests in towers prepared in accordance with the present invention. The plate (11) may be fixed to the tower (10) by any appropriate manner, for example, by screws to the base (13) of the tower (10), or to a support bar above, or in any other manner which does not impede the solution flow. The height of the plate (11) from the base (13) of the tower is preferably 3 to 10 mm, and more preferably 5 mm. The plate (11) may be made of a material which does not interact with the solutions or interfere with the polymerisation reaction, and examples of such materials are poly(methyl methacrylate), aluminium, and stainless steel. The plate (11) should preferably be of a minimum thickness, consistent with strength requirements.

Combined Pretreatment Unit and Gel Forming Container (Reactor Vessel)

Figure 2A:
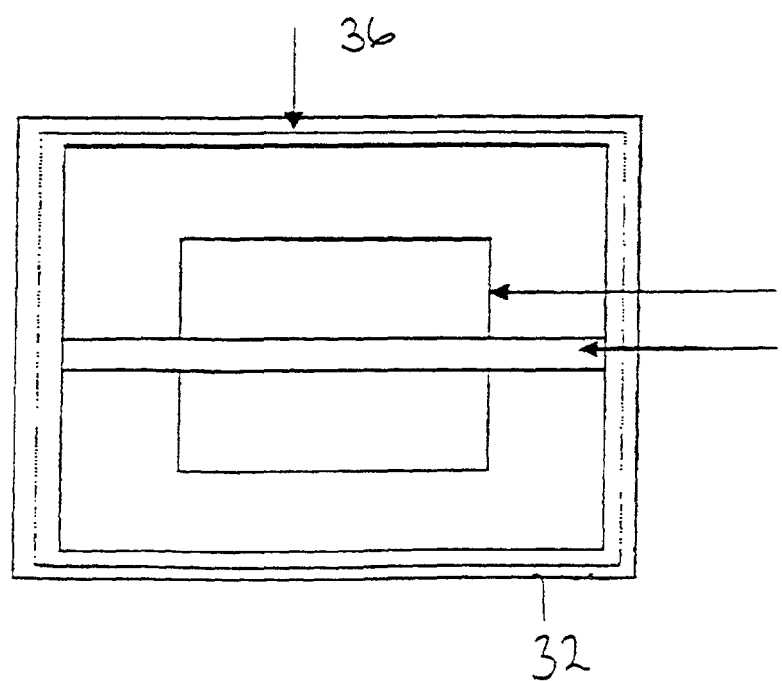
FIG. 2a is a plan view from above of a bottom section of the apparatus shown in FIG. 2.
Figure 2:
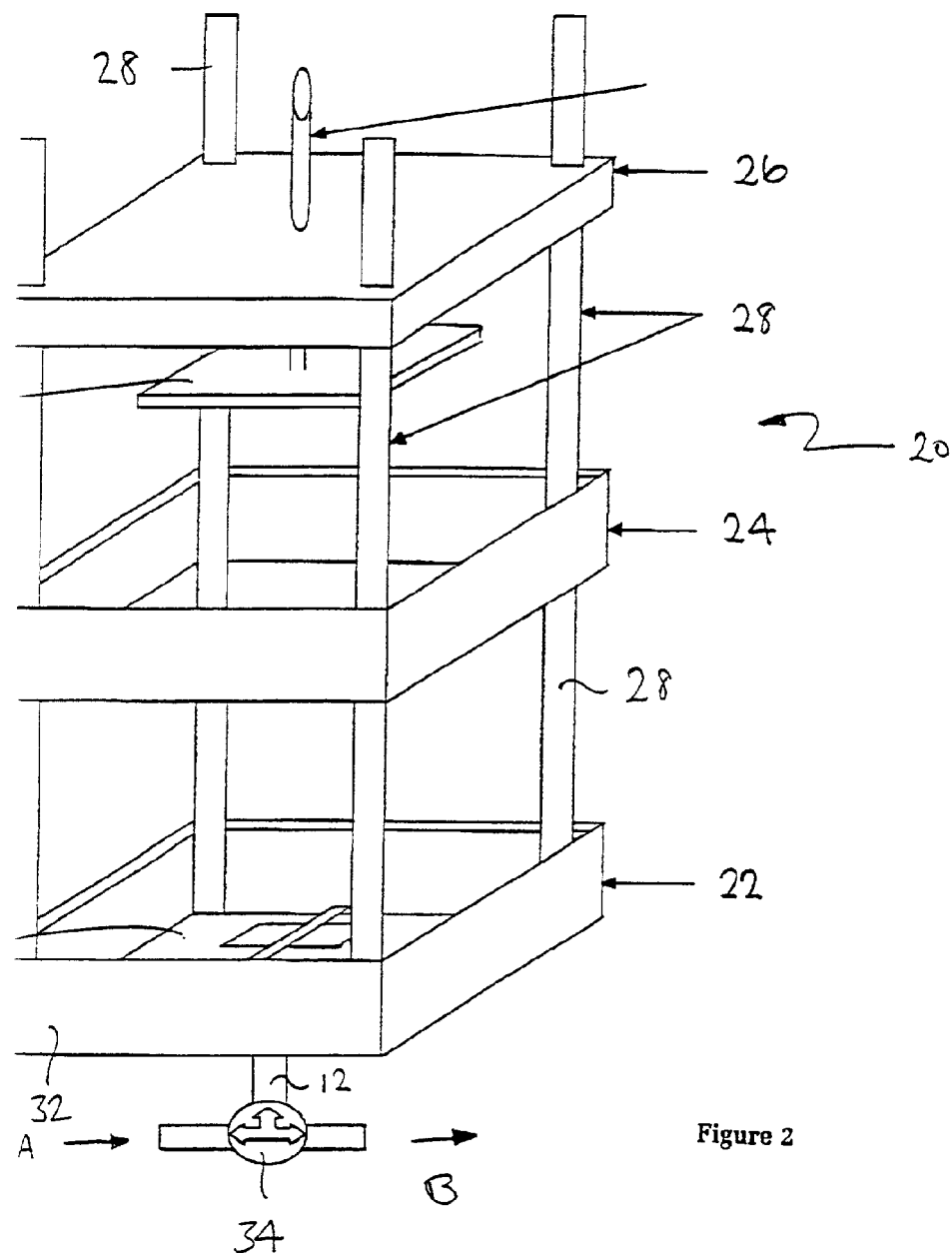
FIG. 2 is a schematic exploded view of a second apparatus embodying the present invention.
Figure 3:
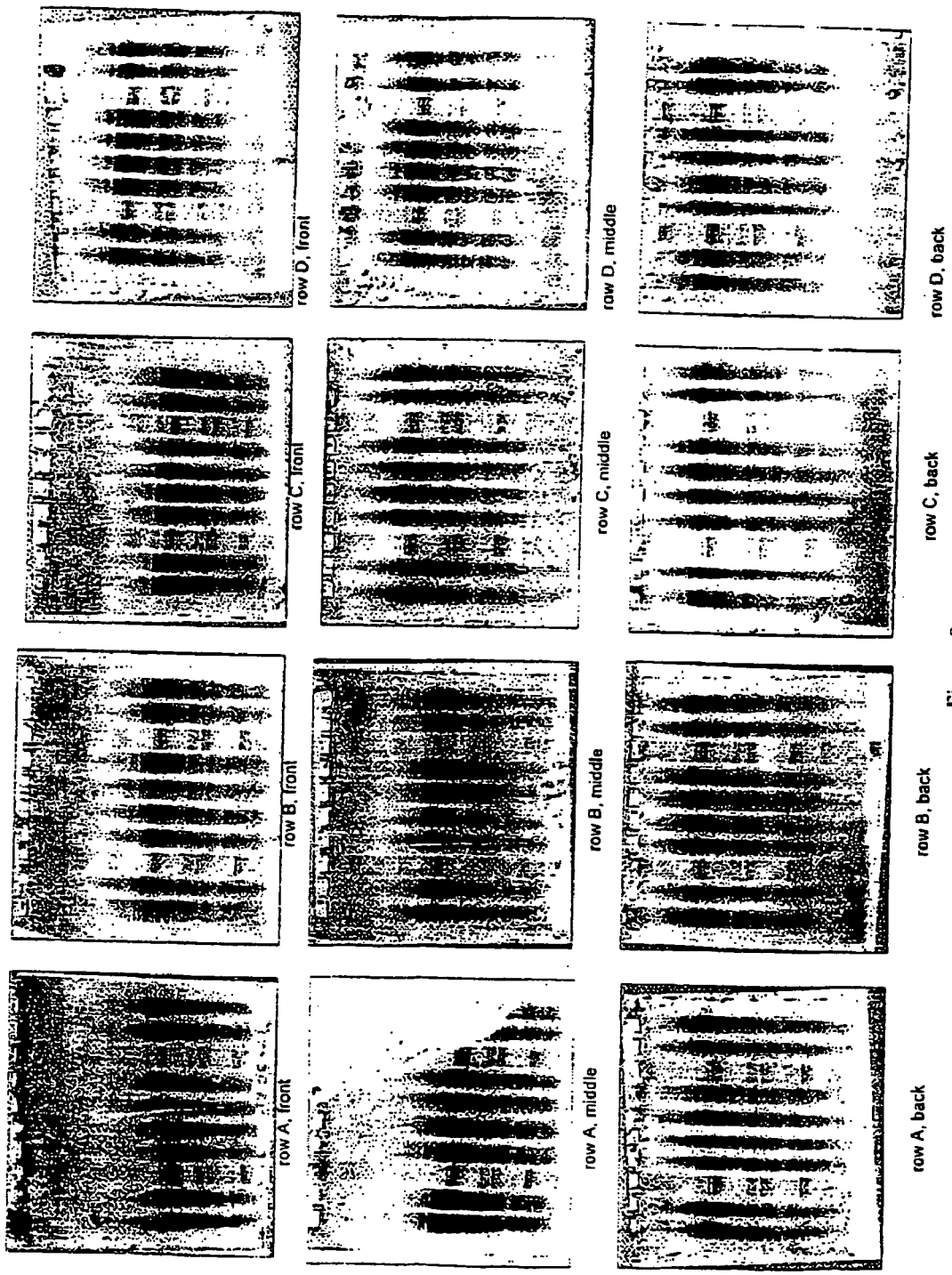
FIG. 3 shows various gels from positions in a gel forming tower shown in FIG. 1a Coomassie blue stained after electrophoresis of protein standards.
Figure 4:
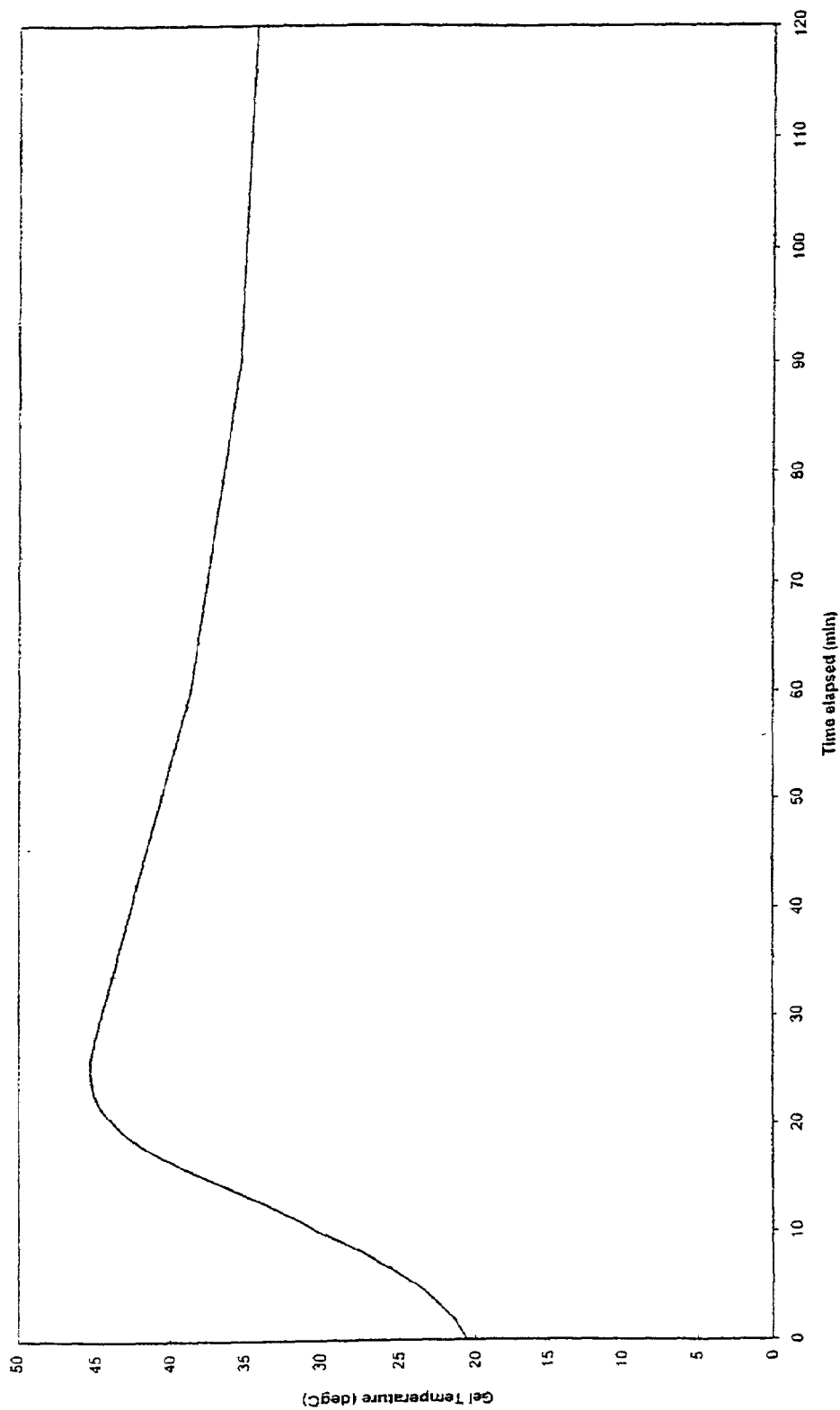
FIG. 4 shows a temperature vs time plot during acrylamide gel polymerisation of a gel positioned at the centre of the gel forming tower during polymerisation.
Figure 5:
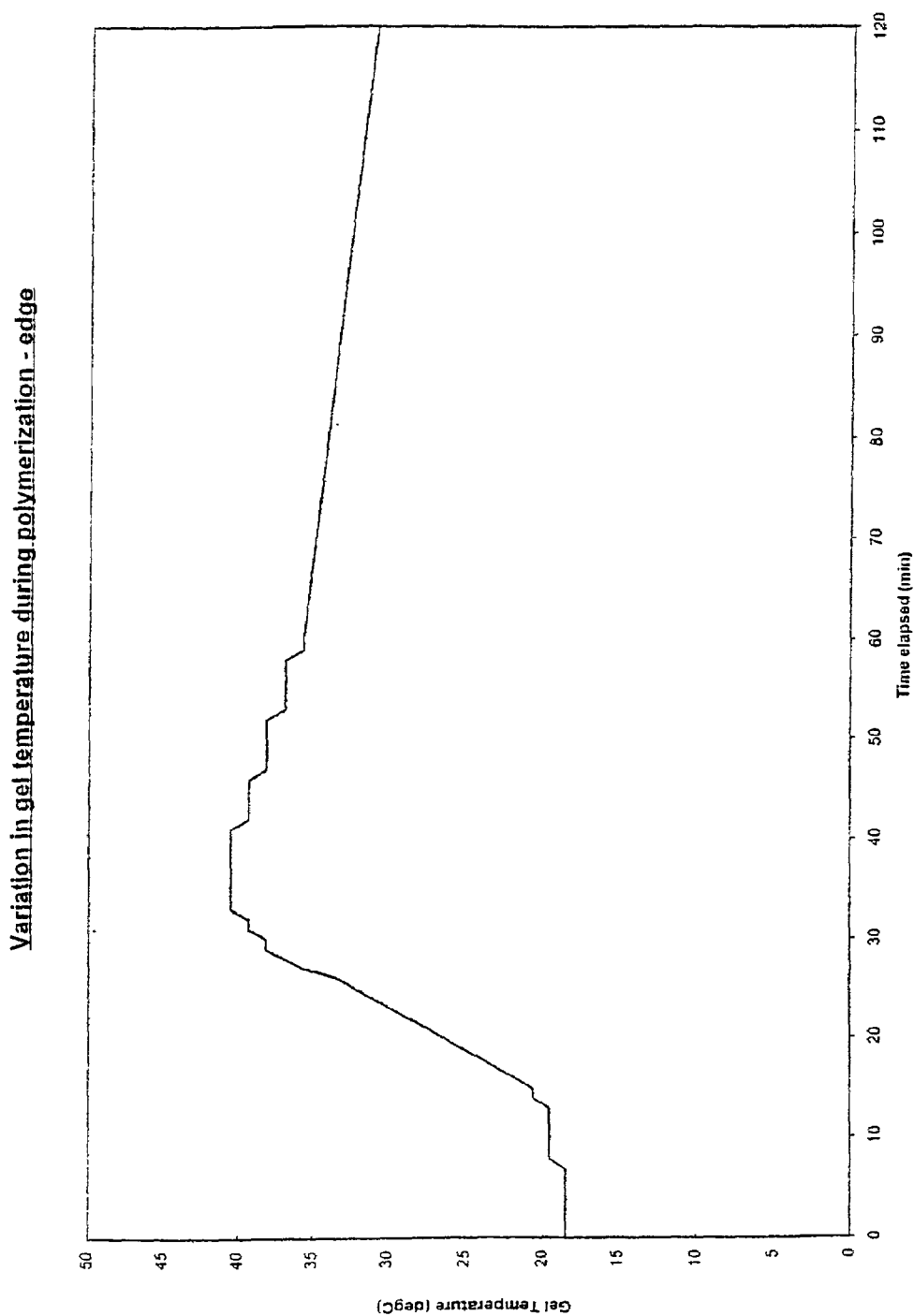
FIG. 5 shows a temperature vs time plot during acrylamide gel polymerisation of a gel positioned at the edge of the gel forming tower during polymerisation.
Figure 6:
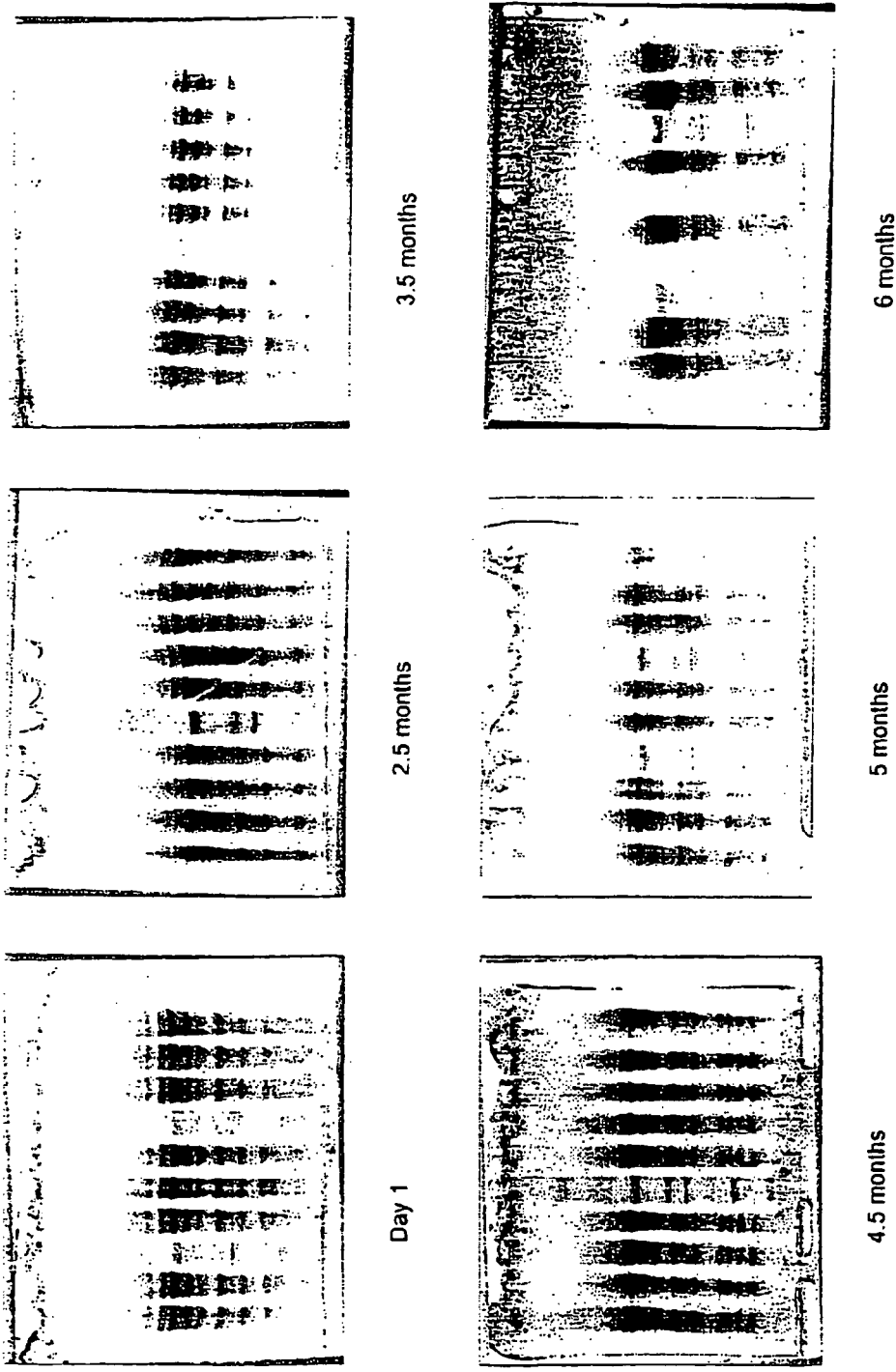
FIG. 6 shows the stability of various gels cast in the one batch and stored over a 6 month period, Coomassie blue stained after electrophoresis of protein standards.
Figure 7:
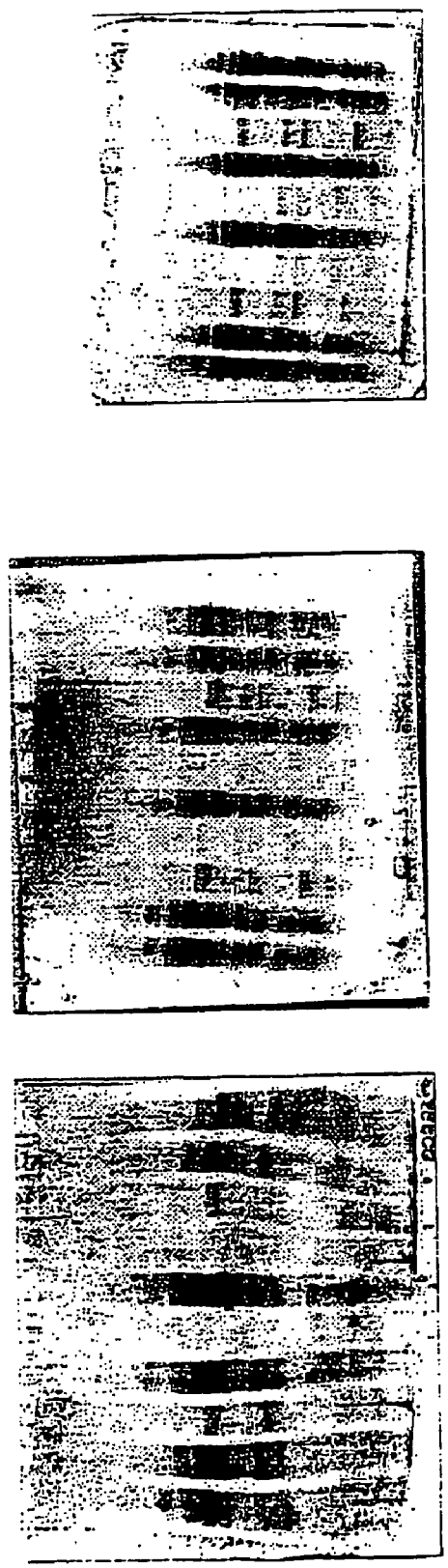
FIG. 7 shows a comparison of two commercial gels with a gel formed by the present invention Coomassie blue stained after electrophoresis of protein standards.
Figure 8:
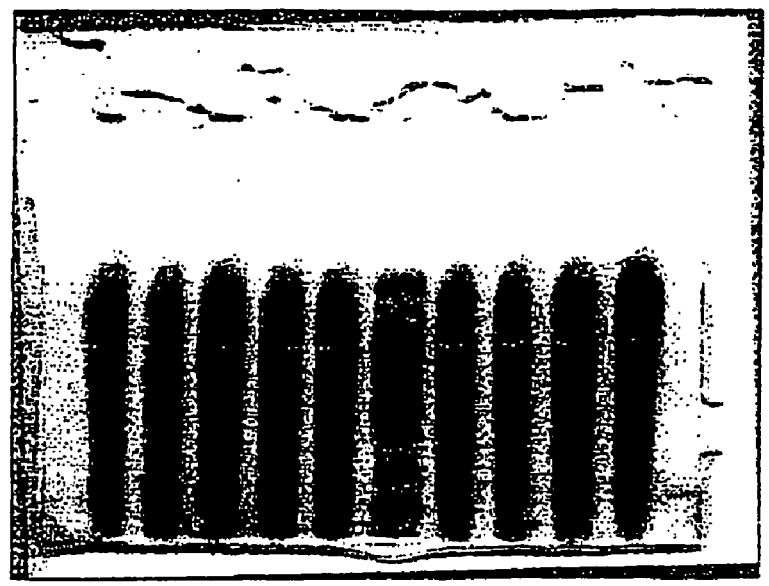
FIG. 8 shows a gel stained using silver diamine after electrophoresis of protein standards.

In an alternative arrangement, the pretreatment unit (vacuum chamber set-up and the gel forming container (tower) may be combined to form a single reactor vessel 20 as shown in FIG. 2. As shown the reactor vessel is formed in three sections which may be assembled to form a gas tight vessel, although two sections or more than three sections could be provided. The preferred vessel as shown comprises three sections being a base 22, a middle section 24, and a top 26. The sections are square in plan view and are mounted on four support poles 28. The sections may be slid apart to allow access inside the reactor and slid together to form a gas tight container. The base 22 has a square floor 30 and side walls 32 and is used to hold the cassettes and admit solutions. A solution inlet port 12 is provided in the floor 30 and covered with a baffle 11 as in the tower shown in FIG. 1. The baffle is mounted on a support beam 16. A valve 34 controls the flow of polymerisation solution A into and waste B out of the reactor. The middle section 24 acts as the body of the reactor and aligns the cassettes. The top section 26 is used to form a vacuum seal by compressing all three sections together. O-rings extend around the edges of the base 22 and top 26 where they face the middle section to form the vacuum seal. A plate is also contained in the top section to assist in maintaining the cassettes in the desired positions and preventing the cassettes from rising when the reactor is filled with fluid. The reactor vessel also incorporates features that facilitate the heating and cooling of the vessel, not shown. The main advantage of this arrangement is the simplification of the manufacturing process, minimising the need for external handling. The reactor vessel is constructed from a material which is suitable for forming a vacuum heating and cooling applications. Suitable materials include aluminium and stainless steel neither of which interfere substantially with the polymerisation reactions. Alternatively, the vessel may be constructed of metals which are coated with substances such as Teflon which do not interfere with the polymerisation reactions.

Synthetic Electrophoresis Gel Supports (Plastic Cassettes)

The cassettes may be manufactured from any suitable synthetic material, such as polyesters (PEN, PET, PETG), polyolefins (polyethylene, polypropylene), polyacrylics (polyMMA) and any copolymers, polystyrene and its copolymers (SAN) and vinylidene chloride copolymers. The different materials, however, may require different levels of pretreatment prior to gel formation. Most plastics may be used, even those previously highlighted as polymerisation inhibiting plastics and unsuitable like polystyrene. In addition, some materials may require further treatment before use. For example, the polyester PEN may require, but not necessarily require, a mild, alcoholic caustic etch prior to use. It will be appreciated that any other pretreatment step which renders the cassette material more useful in the formation of electrophoresis gels would be included in the scope of the present invention.

Scale of Batch Casting

The batch scale may be readily increased without loss of gel quality. Previously, it has been noted that the batch size for the commercial manufacture of polyacrylamide gels is limited by the resultant polymerisation exotherm. The present inventors have been able to improve on the previous maximum batch size of 50, and were able to produce electrophoresis gels routinely in a batch size of 80. In addition, an increase in scale by 4, with a batch of 320 gels has also been achieved. It is surprising that the exotherm under this large scale casting was controllable and relatively uniform across the batch.

The control over the exotherm was evidenced by temperature sensors present within the gel during manufacture at a central and edge position within the batch.

Correspondingly, the gel quality did not vary across the batch and remained consistent due to the ability to control the exotherm. Experiments performed with other plastics gave similar results for exotherm and other properties, and it appears that batch scale need only be limited by physical practicalities.

Process of Manufacture

Initiator Solutions

During the process, there is preferably a sequential addition of the solution components which comprise the monomer mixture. Free radical polymerisation may be initiated by various processes, but from a commercial point of view, the use of a redox system comprising an initiator and a co-initiator is preferred. In contrast to UV photoinitiation or thermal initiation, a redox system is readily adaptable to multiple gel preparations within a batch process. A common redox system is composed of a peroxide based initiator such as ammonium persulphate or potassium persulphate, and a co-initiating agent, which in conjunction with the initiator, is capable of producing free radicals. Examples of co-initiators are N, N, N', N'-tetramethylethylenediamine (TEMED) and 3-dimethylaminopropionitrile (DMAPN).

The process involves the addition of the initiators in a manner such that the minimum holding time is achieved, allowing the solutions to flow into the container and cassettes before the onset of polymerisation. This has the effect of causing:

minimum disturbance of solution flow minimum disturbance of the desired monomer gradient for gradient gels minimum batch rejection due to premature polymerisation The preferred ratio between the initiator and co-initiator components is 1:1. It will be appreciated, however, that other ratios such as 2:1 and 1:2 can be used.

Monomer Solutions

The need to degas the monomer solutions prior to use has long been recognised as a necessary step for the formation of clear and reproducible polyacrylamide gels free of defects. The solutions may be degassed by evacuation using a vacuum pump or water aspirator, or the solutions may be bubbled with an inert gas such as argon, helium or nitrogen, until a very low level of dissolved oxygen is reached.

The use of an improved process incorporating pretreatment of the plastic cassettes, an inert atmosphere for electrophoresis gel formation and degassed solutions enable very low initiator levels to be used when forming the gels in plastic cassettes. Concentrations typically used in acrylamide polymerisation are in the range of 1 to 10 mM. While initiator levels of less than 1 mM are achievable using glass cassettes, the same low concentrations have previously been found not able to yield good polymerisation in synthetic materials without the use of barrier films or chemical scavengers. With this improved process according to the present invention, initiator concentrations of less than 1 mM are routinely used.

The use of low initiator levels has enabled the production of polyacrylamide gels in plastic cassettes with improved qualities with respect to:

control over the polymerisation exotherm storage stability silver staining protein and other biomolecule separation The use of high levels of initiator within the process has been shown to cause the monomer solution to polymerise rapidly, producing an uncontrollable exotherm and brittle gels from the evaporation of water from the gel. Additionally, the incorporation of initiator derived fragments (usually $SO_4{-}$, if persulphate is used) into the polymer chain introduces charged groups into its structure, which is likely to interfere with the separation of biomolecules, affect the level of sensitivity achieved with silver staining, and influence the matrix stability by catalysing hydrolysis.

Therefore, by minimising the presence of oxygen and other volatile inhibitors, the level of initiator may be adjusted down to very low levels while maintaining satisfactory rates of polymerisation for a commercial scale. While the decrease in oxygen has been recognised to increase the rate of polymerisation, previous practice is not to decrease initiator levels accordingly, as the importance of initiator end groups in the polymer structure has not been recognised.

METHODS

Plastic Cassette Preparation

Using SAN cassettes as an example, the pretreatment consisted of subjecting the SAN cassettes to three evacuation/nitrogen purge cycles over a period of 1 hour. Degassing of the cassettes under high vacuum was then left to proceed overnight (12 hours). The cassettes were then subjected to a further three evacuation/nitrogen purge cycles, and then equilibrated to atmospheric pressure under an atmosphere of nitrogen.

Solution Preparation

The required amount of acrylamide and crosslinking agent (generally N, N'-methylene bisacrylamide) to give the desired % T and % C ratio was dissolved in water. To this mixture was added an aliquot of Tris hydrochloride buffer to achieve a final buffer concentration of 0.375M. The solution was then adjusted to pH 8.8 and made up to the final desired volume with water. The monomer solutions were then degassed by bubbling gently with nitrogen gas until less than 1% dissolved oxygen was obtained. Monomer solutions were maintained under an nitrogen atmosphere during gel manufacture.

The water used to prepare the individual components of the redox initiator system, ammonium persulphate and TEMED, was degassed in the same manner. When the desired oxygen level was achieved, the initiator solutions were then prepared.

Gel Preparation

With the aid of peristaltic pumps, the individual monomer solutions, the initiator and co-initiator solutions were pumped into the polymerisation apparatus in a sequential manner. The monomer solutions were mixed in-line first, the co-initiator was then added in-line, and finally, the initiator was introduced in-line, prior to reaching the cassettes within the polymerisation apparatus and vacuum chamber. The initiated monomer solution was then pushed up to the required level in the cassettes with the aid of a salt solution. Once in the cassettes, the solution was left to polymerise under an atmosphere of nitrogen, over a period of 2 hours. Once this time had elapsed, the gels were removed from the tower, and placed into a 60° C. oven for 1 hour for a post-polymerisation curing step. Alternatively, the gels may be left in the tower and exposed to elevated temperatures in situ for curing if required. Once cured, the gels were placed in an 18° C. room, and left to cool to room temperature overnight.

Evaluation of the Resultant Polymer Matrices

Plots were made to show the exotherm is controllable throughout the batch of 320 cassettes (no more than 45° C.).

Quality across the batch is maintained

Storage stability trials showed the gels were capable of a shelf-life of at least 6 months at 4° C., while the shelf-life of other commercially available gels in synthetic cassettes was 3 months at 4° C. Similar gels in glass cassettes have been found to have a shelf-life of 30 days at 4° C.

Separation—was at least equivalent or superior to that of other commercial gels.

Silver staining—was shown to be equivalent to, or better than that of other commercial gels The ability to prepare gels in a variety of different synthetic materials without loss of gel performance was demonstrated.

SUMMARY

Polyacrylamide matrices suitable for electrophoresis were prepared by the present inventors in synthetic gel supports without the use of barrier films or chemical scavengers.

The improved method for the preparation of the polyacrylamide gels according to the present invention can be readily scaled up for mass production in a batch process.

The improved batch process incorporates several features which enabled high quality polyacrylamide gels to be prepared in a reproducible manner using a variety of synthetic supports with minimum batch rejection.

The polyacrylamide gels prepared with the improved process had fewer faults in the polymer structure as there was no or minimal incorporation of oxygen, other inhibitors or initiator-derived fragments into the polymer chain.

As a result, the polyacrylamide gels formed using the improved process had a number of improvements over other gels, with respect to:

control over the polymerisation exotherm
quality
storage stability
separation
silver staining It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An apparatus for forming electrophoresis gels, the apparatus including:
   a container having a base and sides so as to define a chamber therein for receiving a plurality of gel cassettes;
   an inlet port positioned in the base of the container and in communication with the chamber; and
   a baffle positioned over the inlet port, such that, in use, when fluid passes through the inlet port into the chamber, the baffle substantially reduces fluid turbulence and vertical fluid movement in the vicinity of the inlet port during flow of the fluid into the chamber.

2. The apparatus of claim 1 wherein a mesh or honeycomb structure is positioned between the inlet port and the baffle.

3. The apparatus of claim 1 or claim 2 wherein the base of the apparatus is substantially square and the inlet port is positioned in the middle of the base of the container with the baffle placed directly over the inlet port oriented in substantially the same plane as the base.

4. The apparatus of claim 3 wherein the baffle is substantially square having a side length of ½ to ¼ of the length of the sides of the square base.

5. The apparatus of claim 3 wherein the baffle is substantially square having a side length of about ⅓ of the length of the sides of the square base.

6. The apparatus of claim 1 wherein the baffle is substantially flat and is thin in cross-section to minimize flow turbulence as fluid passes around and over the baffle and is disposed between 3 to 10 mm above the inlet port.

7. The apparatus of claim 1 wherein the container defines or forms part of a vacuum chamber the arrangement being such that gel cassettes may be degassed in the vacuum chamber and then filled in situ with initiated monomer solutions arranged to polymerize in the cassettes.

8. The apparatus of claim 7 wherein the container has at least three sections including, a base section including the inlet and baffle, a mid-section and a top section.

9. The apparatus of claim 1 wherein the container is formed from aluminum or stainless steel and incorporates heating and cooling means, such that application and dissipation of heat may be used to advantageously control polymerization in the container.

10. An apparatus for forming electrophoresis gels, the apparatus comprising:
    a container defining a chamber for receiving a fluid, the container further including an inlet port in communication with the chamber for introducing the fluid to the chamber; and
    a baffle positioned relative to the inlet port so as to reduce fluid turbulence and vertical movement proximate the inlet port.

11. A process of forming an electrophoresis gel in a plastic cassette, the process including the steps of:
    (a) pretreating the plastic cassette to substantially remove polymerization initiators present therein;

(b) preparing a monomer solution of acrylamides and treating the monomer solution to substantially remove any oxygen or other gaseous polymerization inhibitors therefrom;

(c) preparing initiator and co-initiator solutions required to induce polymerization of the monomer solution, the solutions being treated so as to substantially remove any oxygen or other gaseous polymerization inhibitors therefrom;

(d) mixing the monomer solution with the initiator and co-initiator solutions to form an initiated monomer solution;

(e) applying the initiated monomer solution to the plastic cassette; and (f) allowing the initiated monomer solution to polymerize in the plastic cassette, wherein steps (e) and (f) of the process are carried out in the apparatus of claim 1.

12. The process of claim 11 wherein steps (e) and (f) are carried out in the apparatus of claim 2.

13. The process of claim 11 wherein steps (a), (e) and (f) are carried out in the apparatus of claim 7.

14. The process of claim 11 wherein the cassettes are made from a synthetic (plastic) material selected from the group consisting of: polyesters (PEN, PET, PETG), polyolefins (polyethylene, polypropylene), polystyrene, and any copolymers (SAN), polyacrylics(polyMMA) and any copolymers and vinylidene chloride copolymers.

15. The process of claim 11 wherein step (a) includes exhaustive vacuum treatment, optionally with inert gas purging.

16. The process of claim 15 wherein the inert gas is nitrogen.

17. The process of claim 11 wherein the duration of the pretreatment step (a) is from 1 to 12 hours.

18. The process of claim 11 wherein steps (e) and (f) are carried out in an inert gas atmosphere.

* * * * *